United States Patent [19]
Naegeli

[11] 3,963,675
[45] June 15, 1976

[54] CYCLOPENTENES, PROCESS THEREFOR AND ODORANT COMPOSITIONS THEREWITH

[75] Inventor: Peter Naegeli, Wettingen, Switzerland

[73] Assignee: Givaudan Corporation, Clifton, N.J.

[22] Filed: July 19, 1974

[21] Appl. No.: 490,166

Related U.S. Application Data

[62] Division of Ser. No. 338,730, March 7, 1973, abandoned.

[52] U.S. Cl............................ 260/598; 260/468 R; 260/586 R; 260/514 R; 252/522
[51] Int. Cl.² ....................................... C07C 47/40
[58] Field of Search ................................... 260/598

[56] References Cited
UNITED STATES PATENTS

| | | | |
|---|---|---|---|
| 2,799,706 | 7/1957 | Kimel et al. | 260/586 |
| 2,870,208 | 1/1959 | Guex et al. | 260/586 |
| 3,743,671 | 7/1973 | Teisseire | 260/598 X |

OTHER PUBLICATIONS

Schutte–Elte, Chemical Abstracts 151632f, vol. 81 (1974).

*Primary Examiner*—James O. Thomas, Jr.
*Assistant Examiner*—G. T. Breitenstein
*Attorney, Agent, or Firm*—Thomas Cifelli, Jr.

[57] ABSTRACT

Cyclopentenes, some of them novel, process for making same and odorant compositions containing them.

6 Claims, No Drawings

3,963,675

CYCLOPENTENES, PROCESS THEREFOR AND ODORANT COMPOSITIONS THEREWITH

This application is a divisional of Ser. No. 338,730, filed Mar. 7, 1973, now abandoned.

FIELD OF THE INVENTION

This invention relates to the field of fragrance.

SUMMARY OF THE INVENTION

The cyclopentenes involved in this invention have the following general formula

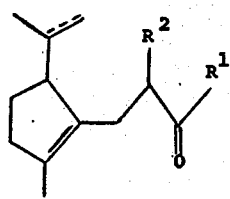

(I)

wherein $R^1$ represents a hydrogen atom or a hydroxy, lower alkyl or lower alkoxy group, $R^2$ represents a hydrogen atom or a lower alkyl or lower alkylidene group and the broken line denotes an optional bond.

DESCRIPTION OF THE PREFERRED EMBODIMENTS

As aforesaid, the cyclopentenes manufactured according to the present invention have the following general formula

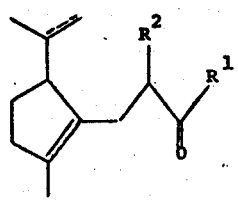

(I)

wherein $R^1$ represents a hydrogen atom or a hydroxy, lower alkyl or lower alkoxy group, $R^2$ represents a hydrogen atom or a lower alkyl or lower alkylidene group and the broken line denotes an optional bond.

In this description and in the accompanying claims, the term "lower" as used in connection with alkyl, alkoxy or alkylidene groups means groups containing up to 6 carbon atoms.

The following cyclopentenes falling within formula I are novel and also form part of the present invention:

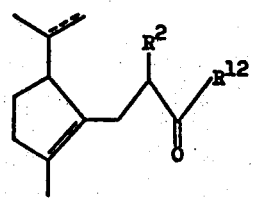

(I-2)

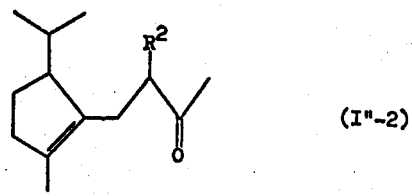

(I'-2)

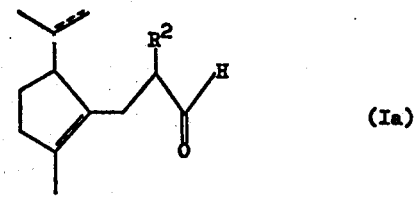

(I"-2)

wherein $R^2$ and the broken line have the significance given earlier, $R^{12}$ represents a hydrogen atom or a hydroxy, $C_{2-6}$ alkyl or lower alkoxy group and $R^{21}$ represents a $C_{2-6}$ alkyl or lower alkylidene group.

Sub-groups of cyclopentenes of formula I-2 have the following formulae:

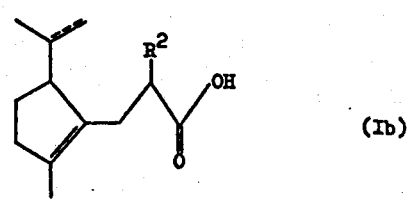

(Ia)

(Ib)

(Ic)

wherein $R^2$ and the broken line have the significance given earlier and $R^3$ represents a lower alkyl group.

The process in accordance with the present invention for the manufacture of the cyclopentenes of formula I comprises reacting a compound of the formula

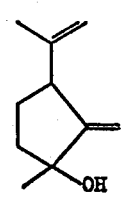

(II)

in the presence of an acidic catalyst with an enol ether of the general formula

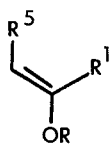

wherein R represents a lower alkyl group, $R^1$ has the significance given earlier and $R^5$ represents a hydrogen atom or a lower alkyl or lower alkenyl group, or a corresponding ketal of the general formula

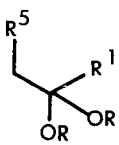

wherein R, $R^1$ and $R^5$ have the significance given earlier,
and, if desired, catalytically hydrogenating a 3-isopropenyl compound of formula I to give a corresponding 3-isopropyl compound of formula I and/or, if desired, oxidising an aldehyde of the general formula

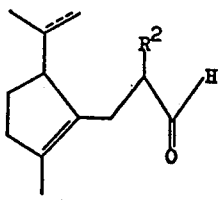

(Ia)

wherein $R^2$ and the broken line have the significance given earlier, to give a corresponding acid of the general formula

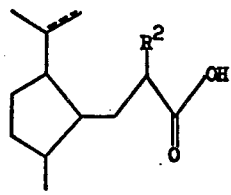

(Ib)

wherein $R^2$ and the broken line have the significance given earlier,
and, also if desired, converting an acid of formula Ib into a corresponding lower alkyl ester of the general formula (Ic)

wherein $R^2$, $R^3$ and the broken line have the significance given earlier.

In the aforementioned reaction it is advantageous to use an excess of an enol ether, with about 3 equivalents being sufficient. If a corresponding ketal is used instead of an enol ether, somewhat smaller yields of the desired cyclopentenes of formula I are obtained.

The reaction is carried out in the presence of an acidic catalyst. As the acidic catalyst there is expediently used a strong mineral acid (e.g. sulphuric acid or phosphoric acid), an acidic salt (e.g. potassium bisulphate, pyridine hydrochloride or mercuric acetate), a strong organic acid (e.g. p-toluenesulphonic acid, oxalic acid or trichloroacetic acid) or a Lewis acid (e.g. zinc chloride or boron trifluoride etherate). The catalyst is expediently present in the reaction mixture in a concentration of from about 0.01 to 1.0%, preferably about 0.1 to 0.3%.

The reaction can be carried out in the presence of, or in the absence of, a solvent. When it is carried out in a solvent, suitable solvents include hydrocarbons such as benzene, toluene, hexane, heptane, isooctane or petroleum ether. According to a particular embodiment, the solvent and/or the alcohol produced during the reaction is distilled off during the reaction.

The reaction is preferably carried out at an elevated temperature (e.g. above 50°C). It is especially preferred to carry out the reaction at the reflux temperature of the reaction mixture. The reaction can be carried out under normal pressure or under excess pressure. The use of an inert gas (e.g. nitrogen or argon) is preferred. In a particular embodiment, the reaction is carried out in an autoclave by heating under an inert gas atmosphere to an internal temperature of about 150°C. The end of the reaction becomes evident by a distinct drop in pressure.

The catalytic hydrogenation of a 3-isopropenyl compound of formula I to a corresponding 3-isopropyl compound can be carried out in a manner known per se. Thus, it can be carried out in the presence of, for example, a noble metal catalyst, preferably palladium or platinum which may be supported on a suitable carrier, preferably on calcium carbonate or barium sulphate.

The oxidation of an aldehyde of formula Ia to give a corresponding acid of formula Ib can be carried out in a manner known per se; for example using Jones reagent ($CrO_3/H_2SO_4$).

An acid of formula Ib can be converted in a manner known per se into a lower alkyl ester of formula Ic.

The cyclopentenes of formula I are distinguished by particular odorant properties, especially by fresh, woody, camphoraceous, spicy, also partially floral, ester-like or weakly sweetish fragrance notes. They can accordingly be used as odorants for the manufacture of odorant compositions such as perfumes and perfume bases or for perfuming technical and cosmetic products of all kinds (e.g. solid and liquid detergents, synthetic washing agents, aerosols, soaps, creams or lotions).

Suitable concentrations of the cyclopentenes of formula I are, in the case of use as an odorant in perfume compositions, 1–30% and, in finished products such as shampoos, soaps, lotions etc., about 0.001–1%.

It will accordingly be appreciated that the invention also includes within its scope (a) an odorant composition which contains as an essential odour-imparting ingredient a cyclopentene of formula I hereinbefore and (b) a method of imparting an odour to materials by applying thereto or incorporating therein a cyclopentene derivative of formula I hereinbefore or of an odorant composition as hereinbefore defined.

The cyclopentenes of formula I are also useful as starting materials for the manufacture of compounds which also possess odorant or aroma properties and which can be used as odorants or as aromatics.

foregoing Formula Scheme into compounds of the spirane or azulene type.

The cyclopentenes of formula III'-1 or III''-1 can be obtained in a manner known per se from the cyclopentenes of formula I'-1 or I''-1 by reaction with an organometallic compound, especially with an alkali metal acetylide or with a Grignard compound of the general formula

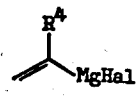

wherein $R^4$ represents a hydrogen atom or the methyl group and Hal stands for a chlorine or bromine atom.

Formula Scheme

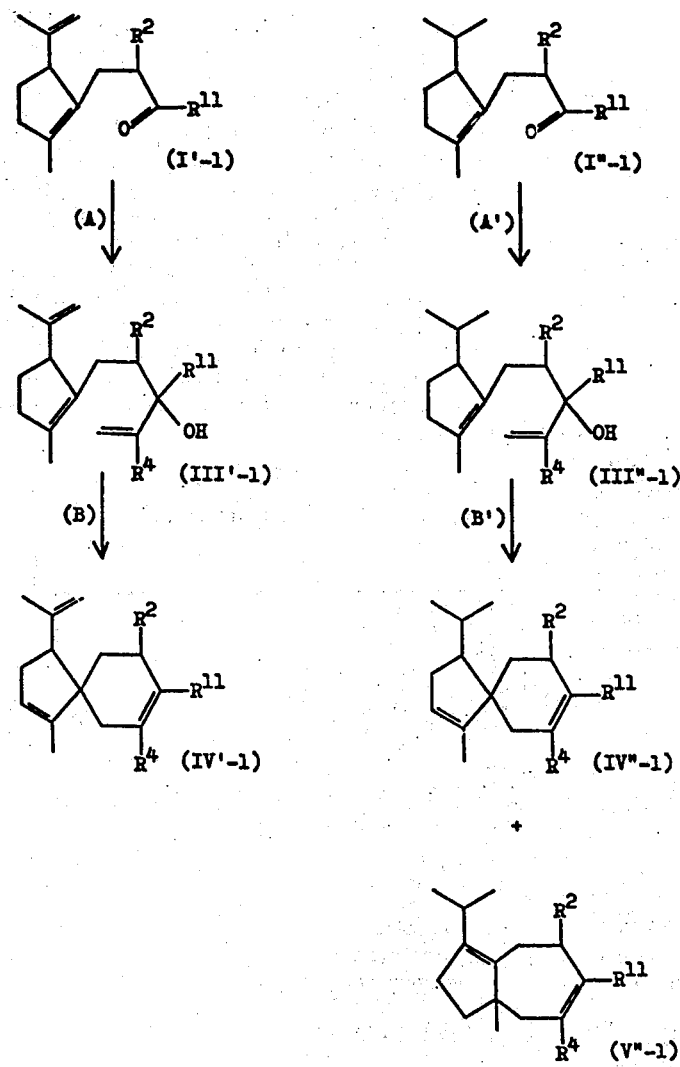

Cyclopentenes of formula I in which $R^{11}$ represents a hydrogen atom or a lower alkyl group (I'-1 or I''-1) can, for example, be converted in accordance with the foregoing Formula Scheme into compounds of the Where the reaction is carried out using an acetylide, it is necessary to catalytically partially hydrogenate the initially obtained compound of the general formula

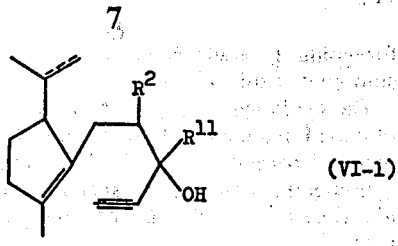

wherein $R^2$, $R^{11}$ and the broken line have the significance given earlier, in a manner known per se; for example, in the presence of a Lindlar catalyst ($Pd/CaCO_3$ deactivated with PbO).

The cyclopentenes of formula III'-1 or III''-1 can then be cyclised-cum-dehydrated to give the compounds of formula IV'-1 or IV''-1. The cyclisation-cum-dehydration can be carried out in a manner known per se. As the cyclisation agent there is expediently used a strong inorganic or organic protonic acid (e.g. sulphuric acid, phosphoric acid, p-toluenesulphonic acid or trichloroacetic acid), an acidic salt (e.g. potassium bisulphate) or a Lewis acid (e.g. tin tetrachloride, aluminium trichloride or boron trifluoride etherate). Suitable solvents include, for example, aliphatic and aromatic hydrocarbons which may be chlorinated or nitrated (e.g. toluene, hexane, heptane or isooctane) or ethers (e.g. diethyl ether, dioxan or tetrahydrofuran). The cyclisation-cum-dehydration can be carried out at a temperature of from about −30°C to about 120°C, preferably at from about 0°C to room temperature.

By-products of the general formulae

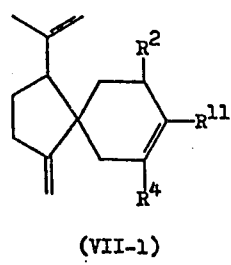

(VII-1)

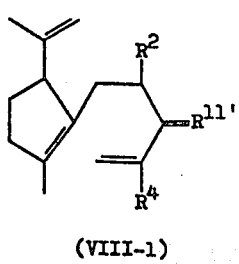

(VIII-1)

wherein $R^2$, $R^4$ and $R^{11}$ have the significance given earlier and $R^{11'}$ represents a $C_{1-6}$ alkylidene group, can result from the cyclisation of a cyclopentene of formula III'-1.

In the cyclisation of a cyclopentene of formula III''-1 there can be obtained, in addition to the compounds of formula IV''-1, compounds of the azulene type of formula V''-1 in yields up to about 70%.

The following Examples illustrate the process provided by the present invention:

EXAMPLE 1

15 drops of 85% phosphoric acid were added to a mixture, cooled in a laboratory autoclave, of 76 g of 3-isopropenyl-1-methyl-2-methylene-cyclopentan-1-ol and 120 g of isopropenyl methyl ether. After gassing with nitrogen, the autoclave was brought, in an oil bath of 180°C, to an internal temperature of 150°C and held at this temperature until a distinct drop in pressure occurred (about 50–75 minutes). The reaction mixture was quenched by intensive cooling, treated with solid potassium hydroxide and concentrated under reduced pressure on a rotary evaporator. By fractional distillation over solid potassium hydroxide there were obtained 58 g (60%) of 3-isopropenyl-1-methyl-2-(3-oxobutyl)-cyclopent-1-ene; boiling point$_{0.01}$ = 69°–72°C; $n_D^{20}$ = 1.4836. The compound has a woody, camphoraceous, ionone-like fragrance.

EXAMPLE 2

4 g of 3-isopropenyl-1-methyl-2-(3-oxobutyl)-cyclopent-1-ene were hydrogenated in 50 ml of ethyl acetate in the presence of 400 mg of palladium on calcium carbonate (5%). After the uptake of one equivalent of hydrogen, the solution was filtered over Celite, concentrated and distilled under a high vacuum. There were obtained 4 g of 3-isopropyl-1-methyl-2-(3-oxobutyl)-cyclopent-1-ene; boiling point$_{0.005}$ about 70°C; $n_D^{20}$ = 1.4709; IR$_{film}$: $\mu_{max}$ = 1725, 1390/70 and 1170 cm$^{-1}$. The compound has a woody, floral note.

EXAMPLE 3

12 drops of 85% phosphoric acid were added to a mixture, cooled to −15°C in a laboratory autoclave, of 76 g of 3-isopropenyl-1-methyl-2-methylene-cyclopentan-1-ol and 72 g of ethyl vinyl ether. After gassing with argon, the autoclave was brought, in an oil bath of 180°C, to an internal temperature of 150°C (this took about 15 minutes) and held at this temperature until a distinct drop in pressure occurred (about 100 minutes). The reaction mixture was then quenched, taken up in ether, washed with aqueous bicarbonate solution and water, the solution dried over anhydrous magnesium sulphate and concentrated under reduced pressure. The crude product (110 g), obtained as a yellow oil, was fractionated and yielded 61 g (68%) of pure 2-(2-formylethyl)-3-isopropenyl-1-methyl-cyclopent-1-ene having a woody, earthy fragrance; boiling point$_{0.2}$ = 64°–65°C; $n_D^{20}$ = 1.4888; IR$_{film}$: $\mu_{max}$ = 3080, 2725, 1725, 1642, 1440, 1370, 1060 and 895 cm$^{-1}$.

EXAMPLE 4

3.6 g of 2-(2-formylethyl)-3-isopropenyl-1-methyl-cyclopent-1-ene were hydrogenated in 80 ml of ethyl acetate in the presence of 500 mg of palladium on calcium carbonate (5%). After the uptake of one equivalent of hydrogen, the solution was filtered over Celite, concentrated and subjected under a high vacuum to a short-path distillation. 2-(2-Formylethyl)-3-isopropyl-1-methyl-cyclopent-1-ene having a fresh, woody fragrance was obtained in quantitative yield; boiling point$_{0.001}$ about 70°C; $n_D^{20}$ = 1.4703; IR$_{film}$: $\mu_{max}$ = 2740, 1728, 1470, 1385, 1368 and 1100 cm$^{-1}$.

EXAMPLE 5

A solution of 25 g of 2-(2-formylethyl)-3-isopropenyl-1-methyl-cyclopent-1-ene in 1200 ml of acetone was treated at −10°C with 55 ml of Jones reagent. The resulting brown mixture was poured on to ice/sodium bicarbonate solution. Ether extraction, washing neutral with sodium bicarbonate solution, saturated sodium chloride solution and water, drying of the extract with magnesium sulphate and removal of the solvent under reduced pressure yielded 20 g (80%) of a weakly yellow oily crude product from which there were obtained by distillation 15 g of pure 2-(2-carboxyethyl)-3-isopropenyl-1-methyl-cyclopent-1-ene; boiling point$_{0.01}$ = 102°C; IR$_{film}$: $\mu_{max}$ = 3600–2400, 1720, 1645, 1450, 1420, 1380, 1330, 1290, 1220, 1085, 945 and 900 cm$^{-1}$. The compound has a woody, spicy, weakly sweetish and somewhat musty fragrance.

EXAMPLE 6

A mixture of 2 g of 2-(2-carboxyethyl)-3-isopropenyl-1-methyl-cyclopent-1-ene, 150 ml of absolute benzene and 4 ml of dimethoxy-dimethylamino-methane was heated for 5 hours to reflux. The solution was concentrated and the residue, obtained as a red oil, chromatographed on 50 g of silicagel with hexane/ether (19:1). There were obtained 1.95 g (91%) of 2-(2-carbomethoxyethyl)-3-isopropenyl-1-methyl-cyclopent-1-ene; boiling point$_{0.01}$ about 70°C; n$_D^{20}$ = 1.4761; IR$_{film}$: $\mu_{max}$ = 3100, 1742, 1645, 1440, 1375, 1330, 1255, 1195, 1170, 1085, 1025, 990, 895 and 840 cm$^{-1}$. The compound has a floral, woody, ester-like fragrance.

EXAMPLE 7

15 drops of 85% phosphoric acid were added to a mixture, cooled to −30°C in a laboratory autoclave, of 76 g of 3-isopropenyl-1-methyl-2-methylene-cyclopentan-1-ol and 130 g of ethyl 1-propenyl ether. After gassing with nitrogen, the autoclave was brought, in an oil bath of 180°C, to an internal temperature of 150°C (this took about 15 minutes) and held at this temperature until a distinct drop in pressure occurred (about 75 minutes). The reaction mixture was then quenched, taken up in ether, washed with aqueous bicarbonate solution and water, the solution dried over anhydrous magnesium sulphate and concentrated under reduced pressure. The crude product (135 g), obtained as a yellow oil, was fractionated and yielded 64 g (67%) of pure 2-(2-formylpropyl)-3-isopropenyl-1-methyl-cyclopent-1-ene having woody, earthy, musty fragrance; boiling point$_{0.005}$ = 51°C; n$_D^{20}$ = 1.4825; IR$_{film}$: $\mu_{max}$ = 3090, 2730, 1735, 1645, 1460, 1380 and 898 cm$^{-1}$.

EXAMPLE 8

In an analogous manner to that described in Example 5, 18 g of 2-(2-formylpropyl)-3-isopropenyl-1-methyl-cyclopent-1-ene were oxidised to 2-(2-carboxypropyl)-3-isopropenyl-1-methyl-cyclopent-1-ene (yield 13.2 g = 68%); boiling point$_{0.005}$ = 110°C; IR$_{film}$: $\mu_{max}$ = 3500–2500, 1705, 1642, 1460, 1440, 1418, 1375, 1290, 1245, 940 and 895 cm$^{-1}$. The compound has a weakly woodily sourish fragrance.

EXAMPLE 9

In an analogous manner to that described in Example 6, 3.12 g of 2-(2-carboxypropyl)-3-isopropenyl-1-methyl-cyclopent-1-ene were esterified. The oily crude product was chromatographed on 100 g of silicagel with hexane/ether (95:1). After distillation in a high vacuum, there were obtained 2.96 g (87%) of pure 2-(2-carbomethoxypropyl)-3-isopropenyl-1-methyl-cyclopent-1-ene; boiling point$_{0.02}$ = 70°C; n$_D^{20}$ = 1.4728; IR$_{film}$: $\mu_{max}$ = 3090, 1740, 1642, 1460, 1435, 1370, 1325, 1285, 1250, 1195, 1170, 1120, 1085, 1060, 1035, 990, 890, 835 and 765 cm$^{-1}$. The compound has a camphor-like fragrance.

EXAMPLE 10

According to the procedure described in Example 7, by the reaction of 30.4 g of 3-isopropenyl-1-methyl-2-methylene-cyclopentan-1-ol with 50 g of methyl (3-methyl-1-butenyl) ether in the presence of 7 drops of 85% phosphoric acid there was obtained 2-(2-formyl-3-methylbutyl)-3-isopropenyl-1-methyl-cyclopent-1-ene in 45% yield; boiling point 0.005 = 55°–56°C; n$_D^{20}$ = 1.4808; IR$_{film}$: $\mu_{max}$ = 3080, 2725, 1725, 1642, 1460/40, 1390/70 and 890 cm$^{-1}$. The compound has a cedar-like, woody, remotely floral fragrance.

EXAMPLE 11

A mixture of 7.6 g of 3-isopropenyl-1-methyl-2-methylene-cyclopentan-1-ol and 8.1 g of 1,1-dimethoxy-3-methyl-3-butene was heated under nitrogen in an oil bath of 100°C for 15 hours in the presence of 100 mg of freshly prepared dry pyridine hydrochloride with continuous removal of the methanol formed. The mixture was then heated for 7 hours to 150°C and finally poured on to a mixture of ice and ether. The ethereal phase was washed with bicarbonate solution and water, dried with anhydrous magnesium sulphate and concentrated under reduced pressure. After distillation of the oily crude product, there were obtained 6.5 g of 2-(2-formyl-3-methyl-2-butenyl)-3-isopropenyl-1-methyl-cyclopent-1-ene; boiling point$_{0.003}$ about 80°C; n$_D^{20}$ = 1.5148; IR$_{film}$: $\mu_{max}$ = 3100, 2780, 1675, 1635, 1440, 1375, 1155, 1060 and 895 cm$^{-1}$. The compound has a woody, floral, fruitily sweetish fragrance.

The following Examples illustrate typical odorant compositions containing the cyclopentenes of formula I hereinbefore:

EXAMPLE A

Composition having a fantasy-floral note:

|  | parts by weight |
|---|---|
| myristic aldehyde 1%* | 5 |
| n-nonyl aldehyde 1%* | 5 |
| lauraldehyde 10%* | 5 |
| ω-n-undecyl aldehyde 10%* | 20 |
| 4-decen-1-al 10%* | 5 |
| jasmine abs. synthetic | 100 |
| phenyl ethyl alcohol | 100 |
| citronellol laevo | 50 |
| linalool | 30 |
| Folrosia Givaudan | 5 |
| storax oil | 15 |
| 7-hydroxy-3,7-dimethyloctan-1-al | 100 |
| eugenol | 25 |
| isobutyl salicylate | 25 |
| isocamphylcyclohexanol | 50 |
| vetivenol | 50 |
| ylang ylang | 60 |
| Absolue Mimosa | 10 |
| heliotropin | 20 |
| civet, natural defatted 10%* | 15 |
| ethylene brassilate 50%* | 15 |
| musk ambrette | 20 |
| bergamotte oil | 100 |
| Absolue Flouve odorante 20% | 70 |
| 2-(2-carbomethoxyethyl)-3-isopropenyl-1-methyl-cyclopent-1-ene | 100 |
|  | 1000 |

*in phthalic acid diethyl ester

EXAMPLE B

Composition of fougere type

| | parts by weight |
|---|---|
| lavender oil cultive | 100 |
| Mousse de Chene soluble | 20 |
| resinoide labdanum | 20 |
| phenyl ethyl alcohol | 100 |
| phenyl ethyl acetate | 50 |
| amyl salicylate | 50 |
| resinoide galbanum | 10 |
| patchouli oil | 20 |
| p-tertbutyl-α-methylhydrocinnamic acid aldehyde | 20 |
| elemi oil | 20 |
| lemon oil Italian | 40 |
| basilicum oil | 5 |
| linalool | 40 |
| bergamotte oil | 50 |
| vetiver oil Bourbon | 15 |
| 2-methylundecanal 1%* | 20 |
| n-undecyl aldehyde 10%* | 20 |
| citronellol | 50 |
| clove oil Zanzibar | 20 |
| 7-hydroxy-3,7-dimethyloctan-1-al | 30 |
| Absolue Flouve odorante 20% | 100 |
| 2-(2-formyl-3-methyl-2-butenyl)-3-isopropenyl-1-methyl-cyclopent-1-ene | 200 |
| | 1000 |

*in phthalic acid diethyl ester

What we claim is:

1. A cyclopentene of the formula

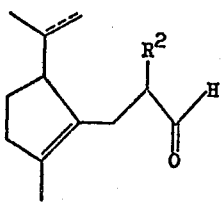

(Ia)

wherein $R^2$ represents a hydrogen atom or a lower alkyl or lower alkylidene group and the broken line denotes an optional bond.

2. 2-(2-Formylpropyl)-3-isopropenyl-1-methyl-cyclopent-1-ene.

3. 2-(2-Formylethyl)-3-isopropenyl-1-methyl-cyclopent-1-ene.

4. 2-(2-Formylethyl)-3-isopropyl-1-methyl-cyclopent-1-ene.

5. 2-(2-Formyl-3-methylbutyl)-3-isopropenyl-1-methyl-cyclopent-1-ene.

6. 2-(2-Formyl-3-methyl-2-butenyl)-3-isopropenyl-1-methyl-cyclopent-1-ene.

* * * * *